United States Patent [19]
Smith et al.

[11] Patent Number: 5,274,327
[45] Date of Patent: Dec. 28, 1993

[54] POWDER SAMPLE HOLDING CAPSULE HOLDING ADAPTER FOR A VIBRATING SAMPLE MAGNETOMETER

[75] Inventors: Mark J. Smith, Rochester; Michael Cellini, Jr., East Rochester, both of N.Y.

[73] Assignee: Xerox Corporation, Stamford, Conn.

[21] Appl. No.: 896,852

[22] Filed: Jun. 12, 1992

[51] Int. Cl.$^5$ .................... G01R 33/12; G01R 33/02; G01N 27/74
[52] U.S. Cl. .................... 324/204; 206/530; 324/226; 324/259; 324/261
[58] Field of Search ............... 324/201, 204, 223, 226, 324/228, 232, 233, 239, 244, 258–262, 377; 206/528, 530

[56] References Cited

U.S. PATENT DOCUMENTS

| | | | |
|---|---|---|---|
| 2,946,948 | 7/1960 | Foner | 324/233 |
| 3,068,380 | 12/1962 | Lamoreaux | 324/377 X |
| 3,904,956 | 9/1975 | O'Brien et al. | |
| 4,037,149 | 7/1977 | Foner | |
| 4,506,221 | 3/1985 | Hayner | |
| 4,804,915 | 2/1989 | Hoenig | |
| 4,996,479 | 2/1991 | Hoenig | |
| 5,001,426 | 3/1991 | Frey et al. | |
| 5,015,953 | 5/1991 | Ferguson et al. | |

OTHER PUBLICATIONS

Stacey et al.; Spinner-magnetometer for thermal demagnetization experiments on rocks, Journal of Scientific Instruments, vol. 36, Aug. 1959, pp. 355–359.
Gill et al.; Teflon and Sapphire Bell for Optical Absorption Studies under High Pressure, The Review of Scientific Instruments, vol. 32, No. 6, Jun. 1961, pp. 752, 753.

*Primary Examiner*—Gerard R. Strecker
*Attorney, Agent, or Firm*—Oliff & Berridge

[57] ABSTRACT

A powder capsule loading system and apparatus for preparing and loading a gelatin capsule with a powder product for testing of the product in a magnetometer. The system includes a gelatin capsule which is readily available, such as those used in the pharmaceutical industry, and a sample tool including a handle section and a cup section which includes an aperture sized to receive part of a capsule portion and holds the capsule portion therein by friction fit. Initially, a top portion of the capsule and a bottom portion of the capsule are each received and held on different sample tools. The capsule portions received within the sample tools are dipped into a sample container of powder product to fill the respective portions with the powder product, followed by assembly of the capsule. The assembled capsule containing a substantially predetermined amount of powder therein is then weighed. If the weighed capsule falls within a predetermined range, the sample is then loaded into an adapter on a vibration sample magnetometer designed for receiving the capsule and subsequently tested for magnetic properties. If the sample falls out of the predetermined weight range, the sample is disposed of and the procedure repeats until a satisfactory testing sample is prepared.

7 Claims, 3 Drawing Sheets

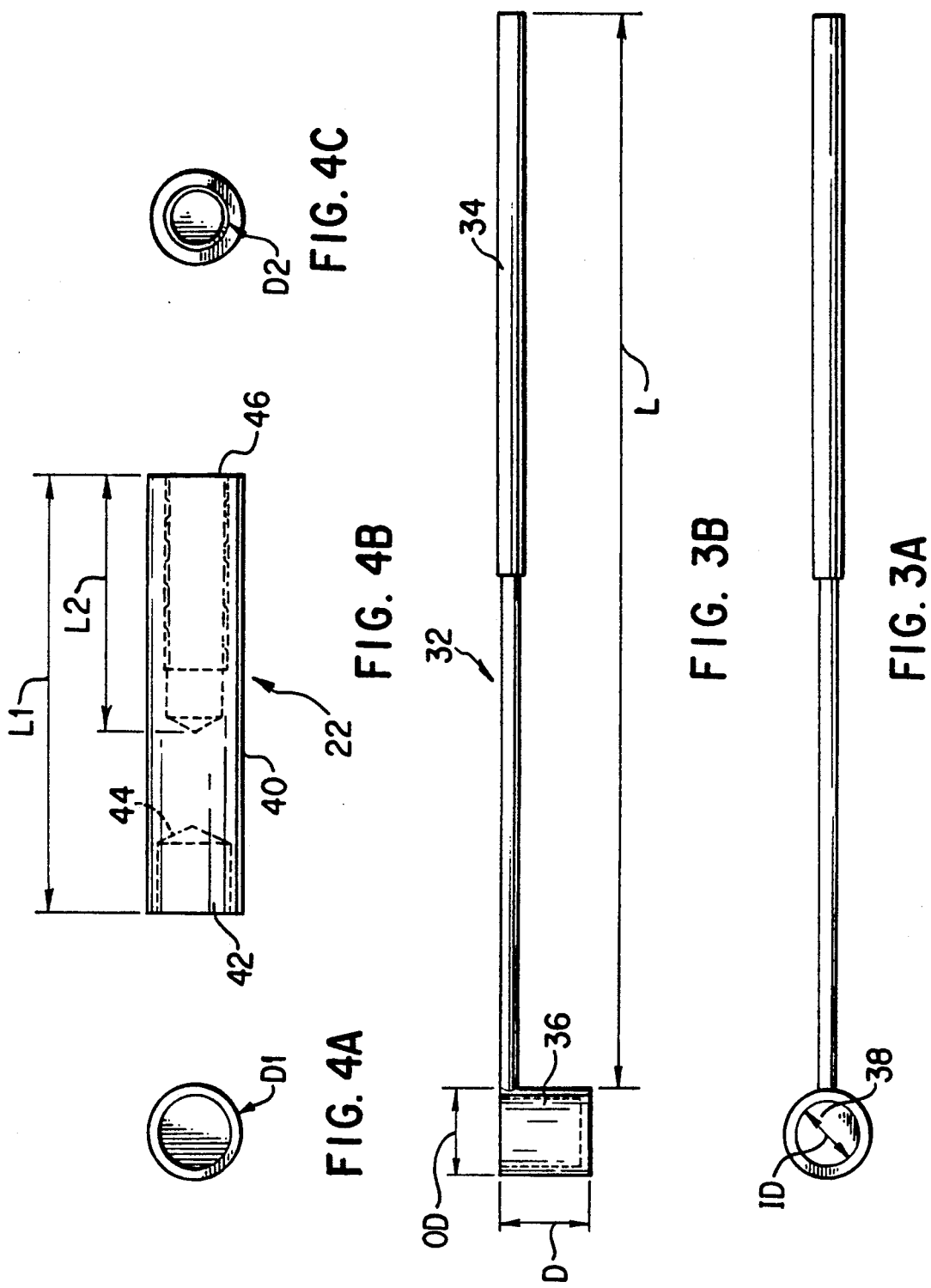

POWDER SAMPLE HOLDING CAPSULE HOLDING ADAPTER FOR A VIBRATING SAMPLE MAGNETOMETER

BACKGROUND OF THE INVENTION

1. Field of the Invention

The present invention relates to a capsule holding and sample handling method and apparatus for obtaining powder samples and making magnetic measurements on a Vibrating Sample Magnetometer (VSM).

2. Description of Related Art

It is highly desirable to test magnetic properties of various powders used in electrophotography. Current magnetic measurements performed on a Vibrating Sample Magnetometer (VSM) are performed in research and development and occasional quality control environments using unique sample capsules available only through a single source. These capsules are extremely expensive.

Present powder sample preparation and loading procedures, which include mounting the capsule containing the test sample in the VSM, necessitated by these capsules are very time consuming, resulting in increased labor costs and a reduction in the total number of samples which can be tested in a day.

There is a need for inexpensive, easily obtainable, disposable powder sample capsules for magnetic measurements on a Vibrating Sample Magnetometer that yield results equal to or exceeding those currently used and an apparatus for adapting such capsules for use on present VSM's.

There also is a need for a loading and testing procedure which reduces preparation and loading times to be more cost effective, reduces labor costs and allows more testing, such that the testing can expand from mainly R&D uses (due to the high cost of the testing) to use in quality control.

OBJECTS AND SUMMARY OF THE INVENTION

It is an object of the present invention to provide a powder sample capsule, capsule holder and loading procedure for use with a Vibrating Sample Magnetometer which is inexpensive, utilizes easily obtainable capsules made by most pharmaceutical companies, and results in reduced sample preparation and loading time.

It is another object of the present invention to provide a capsule holder adapter which easily accepts and holds a standard gelatin capsule by friction fit in one end thereof and can be attached to a Vibrating Sample Magnetometer at the other end thereof.

It is another object of the present invention to provide a capsule tool which easily accepts and holds a standard gelatin capsule by friction fit which can be used to prepare and load a sample amount of a material, such as toner, from a container into the capsule without hand contact with the material.

It is another object of the present invention to provide a system for powder sample measurement which allows a wider range of sample sizes and is inexpensive enough to be disposable.

It is yet another object of the present invention to provide a system for accurate, safe and efficient sample loading and magnetic measurement testing of xerographic materials.

The present invention provides a powder capsule loading system for preparing and loading a capsule with a powder product for testing in a magnetometer. The system includes a capsule which is readily available, such as those used in the pharmaceutical industry, a sample tool including a handle section affixed onto a holder section which receives the capsule in a cavity therein and holds the capsule therein by friction fit. Initially, a top portion of the capsule and a bottom portion of the capsule are each received and held on different sample tools. The capsule portions received within the sample tools are dipped into a container of powder product to fill the respective portions with the powder product, followed by assembly of the capsule. The assembled capsule containing a substantially predetermined amount of powder therein is then weighed. If the weighed capsule falls within a predetermined range, the sample is recorded and stored in an accuvette. Prepared samples can be stored for later use or directly loaded into a VSM for testing. If the weighed capsule falls outside a predetermined range, the sample is disposed of and the procedure is repeated until a satisfactory testing sample is prepared.

These and other objects will become apparent from a reading of the following detailed description in connection with the drawings.

BRIEF DESCRIPTION OF THE DRAWINGS

The invention will be described in detail with reference to the following drawings wherein:

FIGS. 3A and 3B show a preferred capsule tool according to the present invention;

FIGS. 4A, 4B and 4C show a preferred capsule holder adaptor according to the present invention.

DETAILED DESCRIPTION OF PREFERRED EMBODIMENTS

The present invention relates to measurement of magnetic properties of a xerographic material, such as a toner. Typically, this is done using a Vibrating Sample Magnetometer (VSM). An example of such is the Model 155 VSM manufactured by EG&G Princeton Applied Research Corporation, Princeton, N.J. In such a device, a sample of a powder material to be tested is loaded into a special receptacle or capsule and attached to the VSM which then analyzes magnetic properties of the sample, such as measurement of coercivity of powder particle samples. The VSM plots a magnetic hysteresis loop of external field versus induced magnetism.

Presently, unique sample capsules made exclusively for this purpose are the only useable sample receptacles for such a device. These unique capsules are very costly and severely limit the amount of testing which can be performed due to the cost of the capsules. Powder material sample preparation and loading procedures necessitated by these capsules also limit the amount of testing which can be performed due to the labor intensive process.

Figure 1:
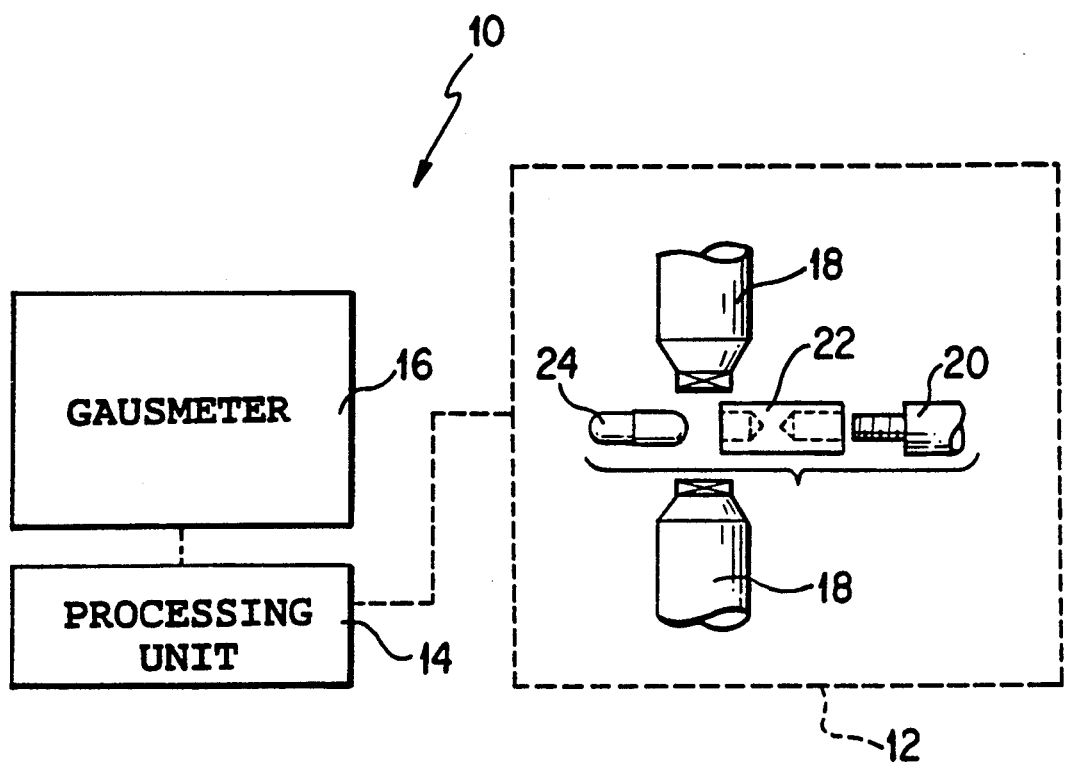
FIG. 1 is a schematic representation of a Vibrating Sample Magnetometer (VSM)

As shown in FIG. 1, a Vibrating Sample Magnetometer 10 includes a magnetic property sensing unit 12, a processing unit 14, a bipolar power supply and Gausmeter 16, and a sample containing region 18 including a threaded rod 20, preferably made of quartz, for receiving a sample holding adapter 22 which places and holds a sample adjacent to the magnetic property sensing unit 12 for testing of the sample.

Figure 2:
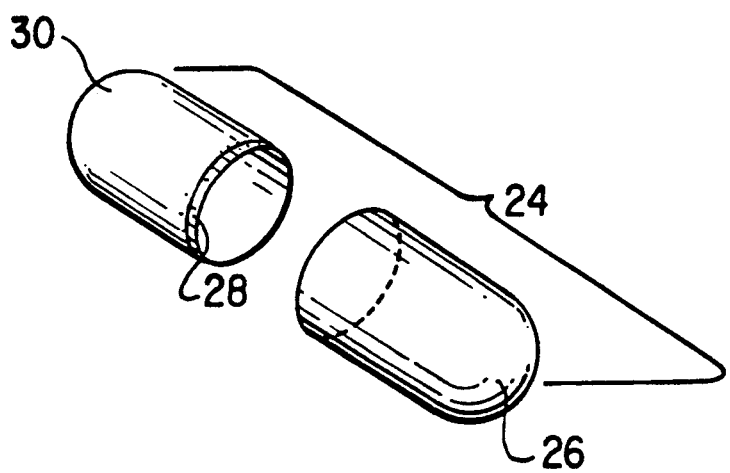
FIG. 2 is a readily obtainable gelatin capsule for use with the present invention.

According to a preferred embodiment, as shown in FIG. 2, the present invention utilizes a standard gelatin pharmaceutical capsule 24 as the sample. This capsule is abundantly available at a minimal cost relative to the present unique VSM receptacle (capsule) for holding material to be tested. A preferred capsule is the Eli Lilly #3 gelatin capsule which consists of a capsule top 26 which is placeable over an edge portion 28 of a capsule bottom 30 to form the capsule 24 which has a curved end profile. The capsule top 26 is shorter and has a larger diameter than the capsule bottom 30. When the capsule top 26 and the capsule bottom 30 mate, the two portions snap together in a relatively tight interfitting relationship.

A novel sample capsule tool 32 for use in handling of the capsule 24 is described with reference to FIGS. 3A and B. The tool 32 comprises a handle portion 34 and a cup portion 36. The cup portion 36 is cylindrical in shape and has a cylindrical cavity 38 therein of a size and a depth to frictionally accept a sufficient portion of the capsule components, i.e., the capsule top or bottom, allowing for easy withdrawal of the capsule portions by a moderate removal force. Preferably, the depth D of the cavity 38 is less than the length of the capsule top 26 or bottom 30. This is preferable such that a portion of the capsule top 26 or bottom 30 extends beyond the cavity 38. When two sample tools are utilized, a capsule top 26 can be inserted in one tool 32 and a capsule bottom 30 can be inserted into a second tool 32. After the test material has been placed in the capsule portions 26, 30, the extended portions of each capsule portion 26, 30 in the tools 32 can be aligned and forced together to form capsule 24 by manipulation of the sample tools 32. The friction force between aperture walls of the cup portion 36 and the capsule portion is sufficient enough to prevent undesired release of the capsule portion during loading procedures (adding test material).

According to a preferred embodiment utilizing a #3 Eli Lilly gelatin capsule, the cup portion 36 has an outer diameter of 0.266 inches (6.76 mm), an inner diameter of 0.219 inches (5.56 mm) and a depth of 0.250 inches (6.35 mm). The inner diameter and the depth define the dimensions of the cavity 38. A preferred length of handle portion 34 is 5.25 inches (133.35 mm) from the cup portion 36 to the end of the handle portion 34. The cup portion 36 is preferably made of brass, although any suitable material, such as a hard plastic, may be substituted.

In a preferred use with an EG&G Vibrating Sample Magnetometer (VSM), an adapter 22 is utilized which attaches to the EG&G VSM machine and receives the sample capsule 24 for testing. As shown in FIGS. 4A, B, and C the adapter 22 comprises a cylindrical rod 40 having cavities 42 and 46 extending into each end thereof. A first cavity 42 is sized to frictionally accept the sample capsule 24 and includes a tapered portion 44 at the innermost part of the aperture 42 which substantially conforms to the shape of the capsule 24 to aid in retaining and stabilizing the capsule 24 in the adapter 22 in a fixed manner. Preferably, when using a #3 capsule, the aperture 42 has a 0.201" (5.11 mm) diameter +/−0.002" and a depth of 0.18" (4.57 mm). The tolerance of the depth is not as critical. On the other end is a second aperture 46, which is tapped to accept a 8-32 threaded shaft 20 of the VSM which connects the adapter 22 with the VSM 10. Preferably, the second aperture 46 is of a depth of about 0.66" (16.76 mm) and contains about 0.50" (12.7 mm) of usable threads. The adapter 22 is preferably made from a 0.25" (6.35 mm) diameter rod of a material which doesn't interfere with magnetic testing and which is capable of being threaded. An exemplary example is KEL-F.

Figure 5:
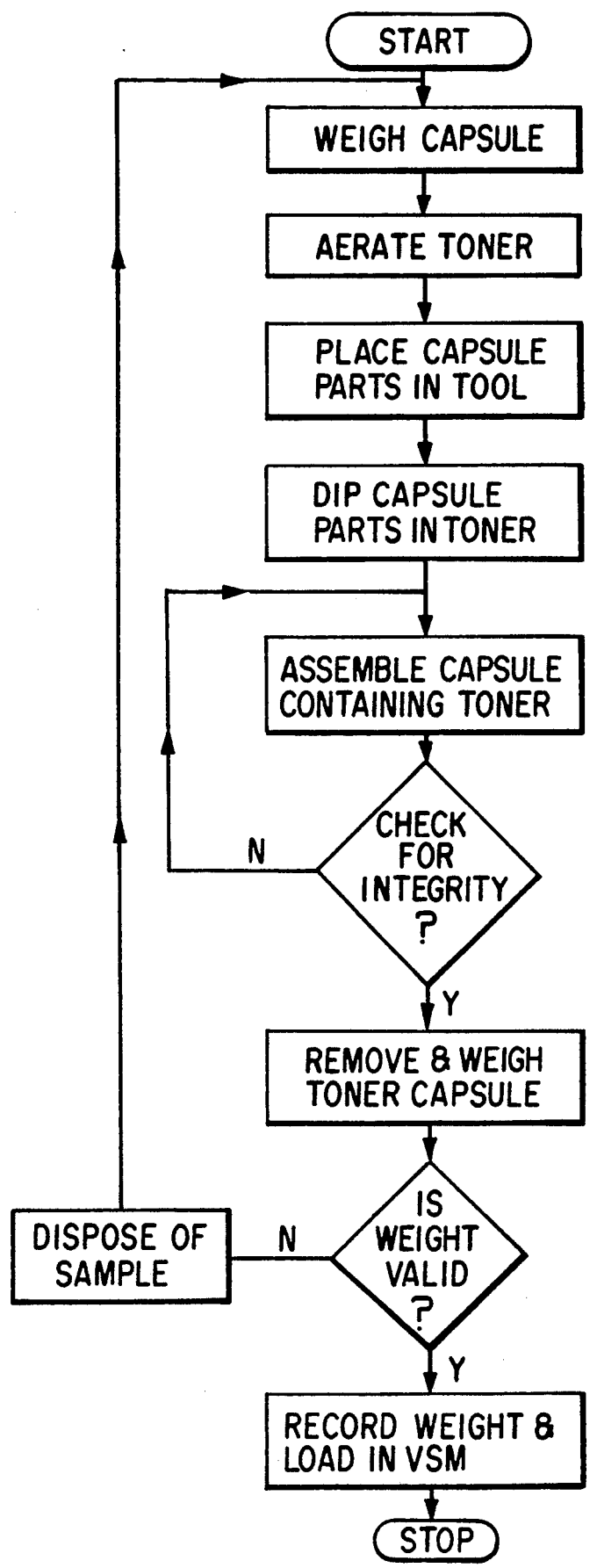
FIG. 5 is a flow chart of a preferred procedure according to the present invention.

In operation, as shown with reference to FIG. 5, the following procedure is conducted to provide an efficient, quality method of loading and inserting the sample into the Vibrating Sample Magnetometer:

(1) The gelatin capsule, including both the capsule top and the capsule bottom, is placed into a weigh boat and both are tared out on a laboratory balance.

(2) A container containing toner powder to be sampled is tumbled to aerate the toner. Preferably, the container is tumbled four rotations. The tumbling may be performed manually or optionally, may be automated.

(3) The capsule top and bottom are each placed in a gelatin capsule sample tool 32 with the open end of the capsule pointing upward and extending out of the cavity in the sample tool.

(4) The gelatin capsule top is dipped in the toner sample container with a first sample tool and lightly tapped to insure that there are no air pockets within the capsule top. Preferably, this to insure that the capsule top is sufficiently packed with toner. The first capsule tool containing the capsule top is then set aside.

(5) Step (4) is repeated with the gelatin capsule bottom contained within a second sample tool.

(6) The gelatin capsule top is pressed over the gelatin capsule bottom using the sample tools. This step reduces hand contact with the test specimens by utilizing the sample tools.

(7) A check is conducted to insure that the capsule top has been "snapped" closed over the capsule bottom. Since both of the sample tools have the same tolerances and since the capsule bottom is of a slightly smaller diameter than the capsule top, when the capsule is assembled, the capsule bottom is easily removed from the second sample tool and the assembled capsule is completed held by the first sample tool.

(8) The sample comprising the capsule top and bottom portion and the toner packed therein is then removed from the first sample tool and weighed.

(9) If the sample weight is between a predetermined range, the sample weight is recorded on an accuvette and the sample capsule is placed into an accuvette.

(10) If the sample weight is not within the predetermined range, the sample capsule is properly disposed of and the procedure is repeated.

Preferably, the sample weight range is between 0.1900 and 0.2900 grams for testing of toner samples on the Model 155 VSM.

Since the gelatin capsules are affected by temperature and moisture extremes, it is preferred that minimal handling of the capsules is performed to reduce chances of sample error in measurements using the Vibrating Sample Magnetometer. Additionally, both the empty gelatin capsules and any loaded sample capsules should be stored in a cool, dry place to reduce deterioration or inconsistent results of the samples.

After one or a sufficient number of capsule samples have been prepared, they may be loaded onto the VSM 10 as shown in FIG. 1 for testing. This loading preferably is performed by manually inserting a capsule sample into the cavity 42 of adapter 22. The adapter 22 is screwed onto the end of the quartz rod (20) and left in place. Once loaded, sample testing can commence as known in the art.

Due to the low cost of the capsules and the simple method of preparing samples, the use of magnetic testing can be expanded to environments outside of just research and development including use in quality control.

The invention has been described with reference to the preferred embodiments thereof, which are illustrative and not limiting. Various changes may be made without departing from the spirit and scope of the invention as defined in the appended claims.

What is claimed is:

1. A capsule holding adapter for frictionally holding an elongated substantially cylindrical pharmaceutical capsule having a predetermined diameter and length in a vibrating sample magnetometer, comprising:
   an elongated substantially cylindrical body having a first and second end;
   a first cavity extending within the first end a predetermined distance, the first cavity being of substantially the same diameter as the predetermined diameter of the capsule to provide a frictional fit of the capsule therein; and
   a second cavity extending within the second end a predetermined distance, the second cavity being threaded and sized to accept a threaded rod from the vibrating sample magnetometer.

2. The adapter of claim 1, wherein the holder adapter comprises a material that does not interfere with magnetic testing.

3. The adapter of claim 1, wherein the first cavity has a diameter sized to frictionally accept a #3 gelatin capsule.

4. The adapter of claim 1, wherein the first cavity has a taper at an innermost end to accommodate a curved end profile of the capsule.

5. The adapter of claim 1, wherein the first cavity has a diameter of about 0.201 inches (5.10 mm).

6. The adapter of claim 4, wherein the first cavity extends within the first end substantially 0.18 inches (4.57 mm).

7. A vibrating sample magnetometer for measuring magnetic properties of a magnetic powder substance, comprising:
   a vibrating sample magnetometer having a threaded rod for attachment with a sample; and
   a capsule holding adapter capable of frictionally holding a cylindrical pharmaceutical capsule of a predetermined size containing a predetermined amount of a magnetic powder substance to be tested, the adapter comprising:
   an elongated substantially cylindrical body having a first and second end;
   a first cavity extending within the first end a predetermined distance, the first cavity being of substantially the same diameter as the predetermined diameter of the capsule to provide a frictional fit of the capsule therein; and
   a second cavity extending within the second end a predetermined distance, the second cavity being threaded and sized to accept the threaded rod from the vibrating sample magnetometer.

* * * * *